United States Patent

Neuberger

(10) Patent No.: US 9,039,684 B2
(45) Date of Patent: May 26, 2015

(54) POWER REGULATED MEDICAL UNDERSKIN IRRADIATION TREATMENT SYSTEM FOR MANUAL MOVEMENT

(75) Inventor: Wolfgang Neuberger, Labuan (MY)

(73) Assignee: Bioliter Pharma Marketing Ltd, Labuan (MY)

( * ) Notice: Subject to any disclaimer, the term of this patent is extended or adjusted under 35 U.S.C. 154(b) by 2585 days.

(21) Appl. No.: 11/443,143

(22) Filed: May 30, 2006

(65) Prior Publication Data

US 2006/0217692 A1    Sep. 28, 2006

Related U.S. Application Data

(63) Continuation-in-part of application No. 10/406,452, filed on Apr. 3, 2003, now abandoned.

(51) Int. Cl.
*A61B 18/18* (2006.01)
*A61B 18/24* (2006.01)
*A61B 18/20* (2006.01)
*A61B 18/00* (2006.01)

(52) U.S. Cl.
CPC ............... *A61B 18/24* (2013.01); *A61B 18/20* (2013.01); *A61B 2018/00196* (2013.01); *A61B 2018/00636* (2013.01)

(58) Field of Classification Search
CPC ............... A61B 18/20–18/24; A61B 2018/2005–2018/245
See application file for complete search history.

(56) References Cited

U.S. PATENT DOCUMENTS

| | | | |
|---|---|---|---|
| 4,846,171 A * | 7/1989 | Kauphusman et al. | 606/15 |
| 5,222,953 A * | 6/1993 | Dowlatshahi | 606/15 |
| 5,437,290 A * | 8/1995 | Bolger et al. | 128/898 |
| 5,531,740 A | 7/1996 | Black | |
| 5,733,277 A | 3/1998 | Pallarito | |
| 6,074,382 A | 6/2000 | Asah et al. | |
| 6,135,996 A | 10/2000 | Kolesa et al. | |
| 6,176,854 B1 | 1/2001 | Cone | |
| 6,231,568 B1 | 5/2001 | Loeb et al. | |
| 6,306,130 B1 * | 10/2001 | Anderson et al. | 606/27 |
| 2004/0092913 A1 * | 5/2004 | Hennings et al. | 606/3 |

* cited by examiner

*Primary Examiner* — Lynsey Crandall
(74) *Attorney, Agent, or Firm* — Bolesh J. Skutnik; B J Associates

(57) ABSTRACT

A system and method for controllably releasing radiation in percutaneous radiation treatment is provided. In a preferred embodiment, a laser is coupled to an optical fiber that is inserted below the skin or into a vascular lumen to a predetermined point. The fiber is connected to a source of electromagnetic radiation such as a laser, non-coherent radiation source, high power laser diode, LED, and an ultrasonic source. Radiation is then delivered to the treatment site while the fiber is simultaneously drawn out to the entry point. The fiber is manually withdrawn and during this time the radiation is administered in a manner appropriate for the vein being treating in regards to power or energy level. To maintain a constant proper energy density, the speed of withdrawal is measured and sent to a controlling mechanism. The controlling mechanism modifies the power emitted, pulse length or pulse rate to ensure that the vein or tissue receives a consistent dose of energy during manual withdrawal. In one preferred embodiment, an imaging device provides the controlling device with position and time information so that speed information from fiber or catheter surface textural properties or based on one or more bar code like markings. In another preferred embodiment, additional information is collected, such as vein diameter prior to treatment, position of the distal end of the fiber, and/or impact measurements such as vibration or temperature during treatment, and the controlling mechanism adjusts output power or pulse rate in response to measurements to maintain a desired power density at all position during the manual withdrawal.

10 Claims, 4 Drawing Sheets

POWER REGULATED MEDICAL UNDERSKIN IRRADIATION TREATMENT SYSTEM FOR MANUAL MOVEMENT

REFERENCE TO RELATED CASE

The present application is a continuation-in-part of Ser. No. 10/406,452, filed Apr. 3, 2003, now abandoned entitled, "Power Regulated Medical Underskin Irradiation Treatment System," by Wolfgang Neuberger.

BACKGROUND OF THE INVENTION

1. Field of the Invention

The present invention relates to the field of underskin radiation therapy. More particularly, the invention relates to power regulated laser underskin or vein therapy.

2. Information Disclosure Statement

Automatic power or wavelength control is known and is utilized in various forms in a variety of laser applications. Such known devices use a variety of parameters by which to control laser energy. It is often advantageous to provide means for regulating radiation parameters, such as power or pulse rate, to ensure a consistent application of radiation or to provide means for altering parameters in response to changing treatment conditions. Inability to properly regulate output power or pulse rate can compromise the safety of a radiation treatment by increasing the risk of perforation, scarring or skin color changes due to energy overdose. Without proper power regulation, the risk also exists of providing insufficient energy, thus insufficiently treating an area and producing the possibility for the need for additional treatments.

Generally, a feedback mechanism is employed that feeds information regarding the treatment site to a controlling unit, which can then adjust the power, frequency or other characteristics of the laser to provide optimal effects. Such feedback information includes measurements of reflected beams, temperature of probes or fibers and temperature of treated or surrounding tissue. Some feedback systems are in place in order to provide constant unchanging radiation parameters, whereas others modify the delivered radiation to maximize therapeutic effect.

For example, U.S. Pat. No. 6,074,382 by Asah et al. discloses an apparatus for ablating epidermal tissue in cosmetic treatments comprising a beam controller and a detector for detecting at least one tissue characteristic (temperature, texture, elasticity, size and shape). The beam controller will alter the beam characteristics based on feedback provided by the detector as to the type of tissue detected. For example, the handpiece may detect color, and the controller may be programmed to only activate a laser over skin marks such as liver spots to avoid ablating healthy tissue. Another example features a second laser beam to relay tissue characteristics to the handpiece to determine whether the tissue should be ablated. This invention is limited to ablative skin resurfacing, and is primarily a scanning apparatus.

Another patent that uses a tissue parameter as a criteria is U.S. Pat. No. 5,531,740 by Black which externally irradiates malformed veins. A detector detects the different color of the veins to restrict radiation to the veins. Reflected light travels from the treatment area to the apparatus, which only allows emission of radiation when the beam is over an area with a predetermined color. This invention involves external scanning over a treatment area and turning the laser on and off to ensure that only veins are treated.

U.S. Pat. No. 6,231,568 by Loeb at al. describes a device and method for forming a channel in heart tissue using both mechanical and laser energy. A needle is used to penetrate the flesh, and a fiber extends further from the needle, followed by irradiation to vaporize tissue and form a channel in the tissue. A device sends position signals to a control apparatus, which indicates when the needle and/or fiber tip has traveled to a predetermined depth. Different energy delivery rates can be selected, but the delivery rate appears to be constant during treatment, and does not vary with position.

U.S. Pat. No. 6,135,996 by Kolesa et al. describes a controlled advancement laser ablation device to be used in performing transmyocardial revascularization (TMR) and angioplasty. In ablation procedures such as TMR, the rate of advancement of the laser fiber is very important yet difficult to control with hand advanced techniques. Kolesa provides a device for automatically controlling the rate of advancement. In this device, the rate of advancement is determined prior to treatment. Devices are also disclosed that limit the depth to which a fiber can travel. This invention is limited to ablation devices and provides a device that features a predetermined power level and advancement speed.

U.S. Pat. No. 6,176,854 by Cone discloses a device and method for underskin treatments utilizing a laser source and optical fiber for the treatment of a variety of skin conditions or for vein treatment. This method does not provide a method of insertion, and does not provide a way to automatically control the laser output depending on the position of the fiber tip. Additionally, power must be manually regulated.

U.S. Pat. No. 4,846,171 by Kauphusman et al. describes an apparatus for advancing and retracting a fiber within a catheter lumen and for controlling energy transmission. The fiber is connected to a sliding mechanism that allows the practitioner to expose the fiber tip from the lumen after the lumen is properly located and thus avoids having to expose the fiber tip before treatment. Also described is a switching means to allow energy to be transmitted through the fiber. Featured is a means to prevent energy from traveling through the fiber if the distal end is beyond a certain preselected point to prevent accidental irradiation while the fiber is inside the lumen. This invention is a positionally dependent laser control, and does not contain means to automatically adjust radiation parameters.

Devices exist for automatically controlling laser power that are dependent on temperature and are thus safety features to avoid over heating irradiated tissue. For example, U.S. Pat. No. 5,222,953 by Dowlatshahi describes an interstitial tumor hyperthermia device for inducing coagulation in tissue. To avoid overheating the tissue, a thermocouple measures the heat of the tissue and prevents over-irradiation of the tissue. In a preferred embodiment, the fiber is withdrawn at a rate sufficient to maintain the temperature of the tissue within a certain predetermined range. A motor is connected with the thermocouple so that it will respond and pull the fiber faster if the temperature gets too high or slower if the temperature gets too low.

U.S. Pat. No. 5,733,277 by Pallarito describes a device and method for ablating vascular or arterial material. The device consists of a laser source, an optical fiber, catheter, and a device for coupling and rotating the fiber. A computer is programmed for the proper movement both rotationally and axially of the optical fiber based on measurements of the obstructing material before the procedure.

A device and method is needed for radiation treatment that prevents under- or over-treatment of an area by effectively regulating the power output or pulse rate of a radiation delivery device based on a number of parameters without dependence on an operator. The present invention addresses this need.

OBJECTIVES AND BRIEF SUMMARY OF THE INVENTION

It is an object of the present invention to provide a device and method to improve therapeutic results of underskin laser therapy.

It is another object of the present invention to provide a device and method to improve the accuracy of underskin laser treatments by removing human error from laser application.

It is a further object of the present invention to provide a device and method that provides for automatic modification of laser power to insure more accurate treatment.

It is still a further object of the present invention to provide a device and method for intraluminal vein treatment that ensures consistent vein irradiation during manual movement, in particular, withdrawal of a fiber.

It is yet another object of the present invention to provide a device and method that automatically adjusts radiation parameters in response to the speed of movement and/or position of a radiation delivery device during manual movement of the optical fiber.

It is still another object of the present invention to provide a device and method that automatically adjusts radiation parameters in response to tissue characteristics and conditions.

Briefly stated, the present invention discloses a system and method for controllably releasing radiation in percutaneous radiation treatment. In a preferred embodiment, a laser is coupled to an optical fiber that is inserted below the skin or into a vascular lumen to a predetermined point. The fiber is connected to a source of electromagnetic radiation such as a laser, non-coherent radiation source, high power laser diode, LED, and an ultrasonic source. Radiation is then delivered to the treatment site while the fiber is simultaneously drawn out to the entry point. The fiber is manually withdrawn and during this time the radiation is administered in a manner appropriate for the vein being treating in regards to power or energy level. To maintain a constant proper energy density, the speed of withdrawal is measured and sent to a controlling mechanism. The controlling mechanism modifies the power emitted, pulse length or pulse rate to ensure that the vein or tissue receives a consistent dose of energy during manual withdrawal. In one preferred embodiment, an imaging device provides the controlling device with position and time information so that speed information from fiber or catheter surface textural properties or based on one or more bar code like markings. In another preferred embodiment, additional information is collected, such as vein diameter prior to treatment, position of the distal end of the fiber, and/or impact measurements such as vibration or temperature during treatment, and the controlling mechanism adjusts output power or pulse rate in response to measurements to maintain a desired power density at all position during the manual withdrawal.

The above, and other objects, features and advantages of the present invention will become apparent from the following description read in conjunction with the accompanying drawings, (in which like reference numbers in different drawings designate the same elements.)

DETAILED DESCRIPTION OF PREFERRED EMBODIMENTS

The present invention provides an effective and reliable method and system for ensuring consistent dosage of laser or other treatment energy to a treatment site during, for example, radiation treatments such as vein treatment or underskin treatments such as varicose vein removal. In such procedures, it is important to deliver a clinically effective dose of energy to tissues without unnecessary damage. It is important to deliver a specific power density, in the case of lasers, or energy amount to tissue, and thus the present invention ensures that the required power density is delivered regardless of the practitioner and thus avoids human error.

For example, the present invention is well suited for endoluminous laser treatments, where a treatment fiber is inserted into the vein or under the skin and laser radiation is emitted at a fixed power setting (for instance 10 W at 980 nm). During irradiation, the fiber is manually pulled out or withdrawn so as to irradiate the desired length of the vessel wall or treatment area. It is evident that the effect achieved will be dosage dependent, and therefore the delivered dosage is dependent on the speed of withdrawal of the fiber through the tissue or vein. Variations in the withdrawal speed may result in undesirable variations in the delivered power or power density and thus variations in the results obtained, such as charring, denaturation and hence imperfect treatment results. Inevitably, variations will occur when the fiber is withdrawn manually, and this is unavoidable as long as the withdrawal speed is controlled by humans. Many practitioners, however, still prefer to be able to manually control such delivery devices to preserve the tactile feel of the procedure and to be able to quickly respond to a patient's reactions. The present invention takes a novel approach by utilizing a device that monitors and changes output, the radiation output, based on withdrawal speed and position rather than attempting to force a steady withdrawal speed.

In a preferred embodiment, the present invention provides a means for measuring the speed of an irradiation means, such as the distal end of an optical fiber, of a radiation delivery device, and feeding that information back to a means to control the power emitted by a radiation source coupled to the delivery device and irradiation means. This system of feedback and control ensures that a consistent radiation dose is applied to all tissue along the withdrawal path of a fiber or other irradiation means connected to the radiation delivery device. For treatments that utilize pulsed radiation, the control unit can alternatively control the pulse rate or pulse length as a function of withdrawal speed and position. By feeding back the speed information to the laser system and controlling the output power as a function of the measured speed and position, improved treatment results can be expected. This measurement and feedback can, for instance, be achieved by encoding the fiber with barcode like markings along a given length of the fiber to be inserted. The movement of these markings past a chosen reference point can then be read by a measurement device to determine the speed of withdrawal and the position on the fiber during the withdrawal process.

The present invention presents another embodiment where a light emitting device is able to determine the position and speed of the optical fiber or catheter, etc., based upon material properties of the optical fiber such as texture. Under ideal conditions, the energy delivered should be uniform along the vein length. The energy delivered is a function of output energy, energy density, position and speed of the output.

In another preferred embodiment, a handpiece or other hollow device is used that is connected to a delivery lumen, such as a needle, to introduce the fiber, catheter containing a fiber, or other radiation delivery device into a tissue or vascular structure. Means to measure the speed of pullback is preferably incorporated onto the handpiece or attached to it, but the measurement means may be incorporated into the system at any desired point along the fiber or catheter length. The optical fiber is optically coupled to a tunable power laser source. Means to control the laser power is coupled to both the measurement means and the laser source. As the fiber is pulled out of the tissue or vascular structure, the measurement means determines the speed of pullback, and sends this information to the control means. The means to control determines the proper emitted power based on preselected protocols, and adjusts the radiation power accordingly.

The means to control may be attached to the radiation or energy source, or remotely connected. In a preferred embodiment, the means to control can be interchangeably connected to different radiation sources. It may preferably be a control unit such as a laptop or desktop computer. The measurement means can be any number of devices, included light-sensitive diodes, in conjunction with markings on the fiber, catheter or other energy delivery device to measure the speed of movement of the fiber or delivery device by the interval between each marking as the delivery device passes through a measurement means. The interval between light blocking markings is sent to the control unit, which calculates the speed and adjusts the power to maintain a proper radiation dosage. In this application, it should be understood that the markings may be placed on the fiber intentionally, for example, or be natural markings, preferably, associated with the texture of the material of the fiber that are essentially periodic in nature. This measurement and adjustment process occurs continually during the treatment process to ensure that variations in pullback speed are accounted and corrected for. Alternatively, the periodic markings described above may be highly reflective to the LED radiation, laser radiation, or other light sources. The light sensitive diodes or other measurement means can then be used to measure the interval between markings by recording the interval between higher measured light intensities due to the reflective markings. The control unit then adjusts radiation or energy output based on the speed calculated from those intervals. The marking may be on any number of devices, including optical fibers and catheters of different sizes and lengths for delivering radiation or other energy for coagulation or therapy.

Another embodiment of the measurement means is an optical speed and position measurement device through which the radiation delivery device, including an optical fiber or a catheter, can be advanced or withdrawn. In this embodiment, the measurement means consists of an illumination source such as an LED or a laser diode, an imaging device, image processing means, and means to relay speed or position information to the control device. The measurement means is preferably stationary. The measurement means may be incorporated into a handpiece such as described above. In a preferred embodiment, the measurement means is positioned around a transparent tube through which the radiation delivery device is advanced or withdrawn. The measurement means in practice operates similarly to an optical mouse often used with personal computers. The illumination source illuminates the surface or other textural features of the delivery device and the imaging means takes a series of images of the surface. Based upon changes in the textural features of the delivery device surface, the measurement means determines the speed, position, and direction of movement of the delivery device. From this information, and based on position information entered at the beginning of a procedure, the measurement means can also determine the position of the irradiation means such as a bare fiber tip or a diffuser. This information is continually relayed to the control unit which can then alter the radiation dose or provide the information to a user. Bar code like markings, as described above, can also be used in conjunction with this embodiment although a standard optical fiber having one or more bands thereon is operable with the optical mouse like device of the present invention. Such external markings also provide visual information to the operator as the fiber or catheter is moved.

A further embodiment of the present invention features the inclusion of a drawing motor in addition to the measurement means and control unit. In this embodiment, the control unit, based on speed and power information, controls both the speed of the withdrawal and the emitted power, to allow further control over the procedure. A drawing motor is included for automated withdrawal of the catheter or optical fiber, and is controlled by the control unit based on information from the measurement means. The motor can maintain the withdrawal at a constant speed, or vary withdrawal based on a number of parameters. An example of one parameter is vein diameter, wherein the radiation power is kept constant and the control unit varies the withdrawal speed as the vein diameter changes to maintain a constant power density. Other parameters include power emitted by the radiation source, wherein the control unit calculates and maintains the proper withdrawal speed to produce a given power density. The power density may be constant or may vary depending on the needs of the treatment or desires of the user. The user may also prefer to use a combination of varying withdrawal speed and radiation power, for example, to minimize treatment time. The motor may also be controlled to withdraw the catheter in user defined steps, if it is desirable to avoid irradiating the whole vein in one withdrawal step. In one example, the control unit directs the motor to withdraw the fiber in defined increments. The motor withdraws the catheter or optical fiber a given length increment (10 mm, for example), irradiates the section of vein, then withdraws another increment, performs the next irradiation, and so on.

An additional safety feature can be realized by the addition of the motor. The control unit can be programmed to stop withdrawal if the force required by the motor exceeds a given level, so that the treatment can be automatically stopped if a problem occurs. Additionally, an alarm or other audible or visual means is included to alert the user if there is a problem. Such a problem may include instances where the optical fiber sticks to coagulated tissue. Also, the motor can be useful in instructing a newer user as to the proper withdrawal speed for a given treatment. The control unit can perform the treatment, after determining the correct withdrawal speed based on the desired power density and given radiation power, by using the motor to withdraw the optical fiber or catheter at the correct speed. A newer user can observe and learn the correct withdrawal speed where manual withdrawal is desirable for a later treatment.

This embodiment, which includes a drawing motor as described above, is particularly useful with the optical mouse embodiment. The optical mouse can serve as an additional safety feature by providing continuous measurements of speed and position to verify the correct position and that the motor is withdrawing at the correct speed. The control unit can use this feedback information to control the motor and maintain the desired power density.

In some applications of the present invention, there may be a desire to alter the parameters of the energy source based on position of the fiber, the type of blood vessel, or to provide a treatment in which the power changes based on the progression of the treatment. For example, a preselected "power step ladder" could be programmed into the control device (such as 13, 10, 7, 5, and 3 Watt levels). The control unit would progress to each level as the treatment progresses or vary as the vein diameter significantly changes. Prior to treatment, the practitioner would enter information such as the size of the vein at the distal starting point, the size of the vein at the proximal end of the vein, and the length of the vein to be treated. The control unit could then change the power output of the source based on the percentage of vein length that has been treated. This device could be used to treat all types of veins, including branches and reticular veins.

As previously described, the present invention controls radiation power based on preferred radiation dose information as entered into the control unit prior to treatment. In another embodiment, the control device uses information provided from previous treatments to determine proper radiation doses. In a "learning mode", the control device learns from information received during treatments by experienced practitioners. For example, the measurement means and control unit is fitted onto an introducer handpiece, and information regarding the type of treatment, size and location of the vascular lumen, radiation parameters (such as wavelength), and diffuser or fiber type is entered into the control device. The practitioner then performs the treatment based on prior experience. The measurement means measures the speed of the fiber and the control unit determines the proper radiation dose, or "expert" condition, based on the treatment parameters. This information is then stored for future treatments. For later treatments, the treatment information is entered as before, and the control device monitors the treatment by either automatically adjusting the delivered power to maintain the proper dosage or by prompting the user to, for example, speed up or slow down withdrawal to permit the "expert" condition to prevail.

In an alternative embodiment, the control unit provides dose information to the user instead of automatically altering the delivered power to maintain a desired dosage. This information could, for example, be acoustical feedback, such as an alarm that goes off when the user is straying from a predetermined dose range, or a graphical display that the user could monitor. Either of these methods of providing information would be utilized by the user to adjust the speed of advance/withdrawal to maintain the radiation dose to within proper levels.

The present invention is not limited to laser applications, but is also useful for other means of coagulating tissue. For example, radio frequency sources can be used in a variety of applications to treat numerous areas of the body. Also, ultrasonic sources may also be used with the present invention for coagulation of tissue. The principles described above in the context of laser therapy are equally applicable to the above therapeutic electromagnetic radiation sources.

The present invention is likewise not limited to speed-dependant power regulation. There are a number of measurable parameters that can also be monitored either before or during treatment to insure that an effective dose of radiation is applied to a treatment area. Prior to activation of a radiation source, measurement of the position of the irradiation means such as a fiber tip or diffuser can be taken to ensure that the proper area is being irradiated. In a preferred embodiment, the light blocking marks used for speed measurement above may also be used to measure the position of the irradiation means by calculating the length of an optical fiber that has been advanced through a vein or tissue. Other pre-treatment parameters include measurement of vein diameter, which is relayed to the control unit for calculation of emitted power to ensure proper power density.

During treatment, it is desirable to monitor the condition of the irradiated tissue by measuring the impact of the radiation on the tissue to prevent over-irradiation. Such impact measurements include the measurement of sound, vibrations, temperature and other conditions that would be relevant to determining whether the tissue has been desirably affected. For example, a means for measuring the temperature of tissue would be useful for determining whether a vein has been denatured/destroyed. A temperature-sensing means can be positioned on the distal end of an optical fiber to relay temperature measurements to the control unit. The control unit can compare the measurements with the known temperature required to destroy/denature the vein, and adjust power or pulse rate to achieve the temperature or avoid overheating the vein and damaging surrounding healthy tissue.

Figure 1:
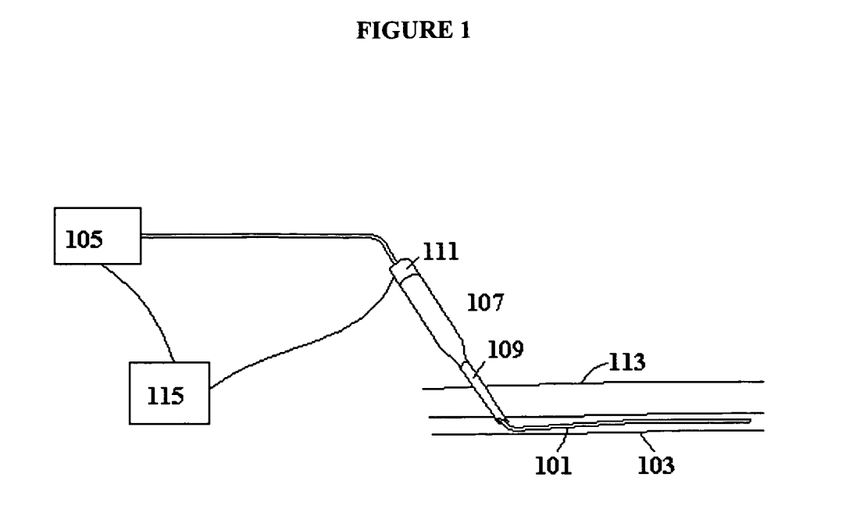
FIG. 1 illustrates a system of the present invention.

A preferred embodiment of the system described in the present invention is illustrated in FIG. 1. In this example, optical fiber 101 is used to deliver radiation to vein 103. Fiber 101 is optically coupled to tunable laser source 105, and fed through handpiece 107. Handpiece 107, in this embodiment, further consists of needle 109 and measurement device 111. Fiber 101 is fed through handpiece 107 and through skin 113 into vein 103 by way of needle 109. The system also includes control unit 115, which is preferably a microprocessor or computer. Control unit 115 is connected to both measurement means 111 and source 105. As fiber 101 is withdrawn by a practitioner, i.e., having an output tip 120, position and speed of movement information of such is sent from measurement means 111 to control unit 115. This information is used to determine the desired power level based on treatment protocols entered into control unit 115 before treatment. If the emitted power is different than the desired power as calculated by control unit 115, the power is adjusted to match the desired power.

Figure 2:
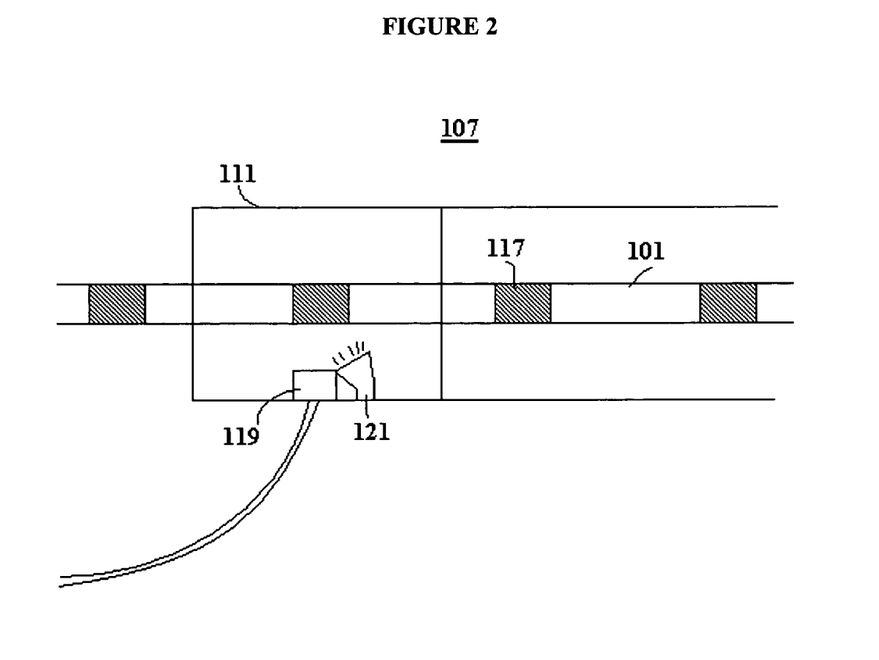
FIG. 2 illustrates a two-dimensional side view of one embodiment of measurement means.

Another embodiment of measurement means 111 is illustrated in FIG. 2. Fiber 101 contains a plurality of dark colored markings, or bars 117. Light detector 119, which can be a light-sensitive diode, is positioned near fiber 101, and light source 121 is positioned to shine low power light onto fiber 101 to be reflected and sensed by detector 119. Light source 121 can be a lamp emitting white light or an LED or a laser diode. As fiber 101 passes source 121 and detector 119, bars 117 alter the amount of light that is reflected and detected. These changes in the amount of reflected light, and the interval between such changes due to bars 117, are relayed to control unit 115 for pullback speed determination.

Figure 3A:
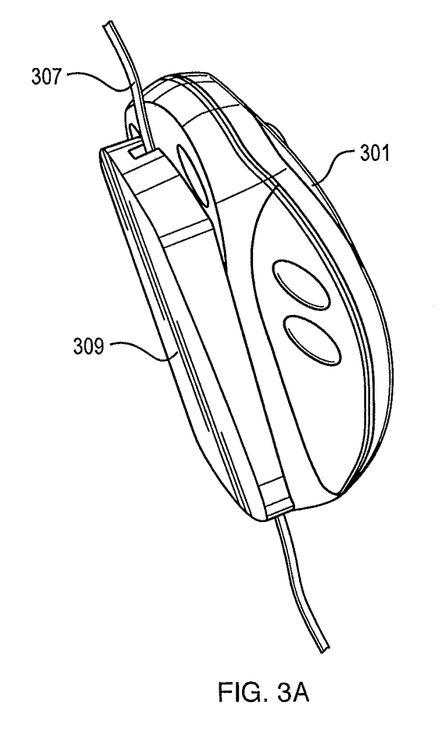
FIG. 3A illustrates a view of a preferred embodiment as assembled.
Figure 3B:
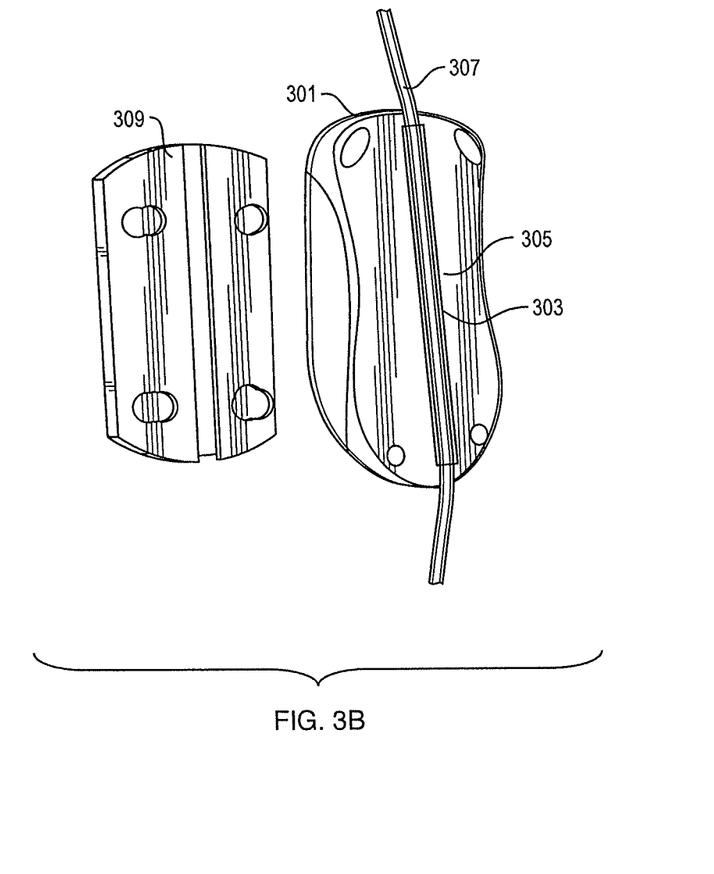
FIG. 3B illustrates a view of the unassembled preferred embodiment of FIG. 3A.

Another preferred embodiment of the system described in the present invention is illustrated in FIGS. 3A and 3B and described as follows: The measurement means consists of optical mouse 301 appropriately modified to implement the present invention by attaching transparent glass tube 303, FIG. 3B, affixed under optical sensor 305. Catheter 307, which contains an optical fiber, not shown, for transmitting radiation from a laser into a vein, extends from a treatment radiation source, is fed through glass tube 303, and extends into the handpiece or other means for inserting the catheter or optical fiber into the vein. During treatment, the optical fiber is locked inside of the catheter 307. Optionally, base plate 309, FIG. 3A, which is shaped to accommodate the mouse underside and glass tube 303, is attached to the underside of mouse 301 and tube 303. Base plate 309 allows the measurement means to be easily placed on a surface such as the surface of the patient's skin near the vein to be treated and further protects the position of glass tube 303 thereon. The bottom of base plate 309 may be flat or shaped to conform to the surface upon which it rests. Base plate 309 and tube 303 are appropriately modified for different sizes of tubes because of different sizes of fibers, catheters, etc.

Catheter 307 can then be advanced or withdrawn through the vein while the measurement means is stationary, and optical mouse 301 can detect the movement and transmit position and movement information to a computer. Based on previously entered treatment parameters, the computer adjusts the power level of the laser to ensure consistent radiation dosage. Additionally, vein diameter can also be taken into account in determining proper radiation dose. The vein diameter upon insertion of catheter 307 into the vein is entered into the computer, and catheter 307 is advanced into the vein. At each desired position, the user clicks mouse 301 and enters the vein diameter at that position. The computer stores the vein diameter and position information at each entered position. Upon withdrawal, the computer calculates the power level at each position based upon the withdrawal speed of catheter 307 and the diameter of the vein at each position.

Figure 4A:
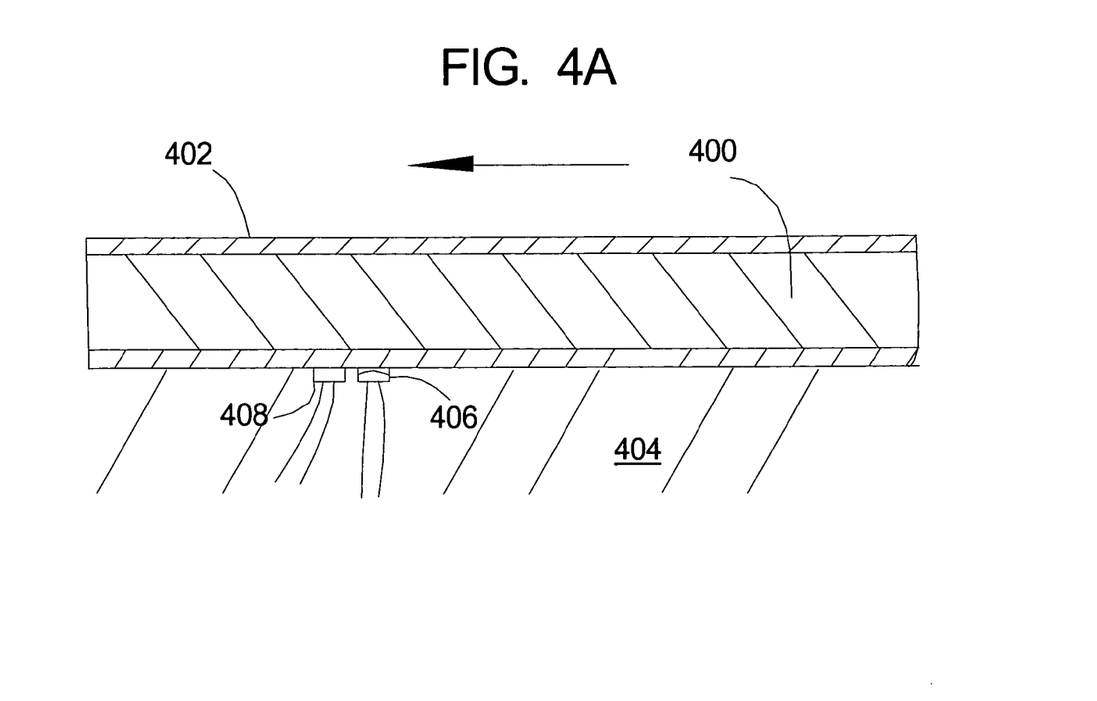
FIG. 4A illustrates a two-dimensional side view of another embodiment of the measurement means.
Figure 4B:
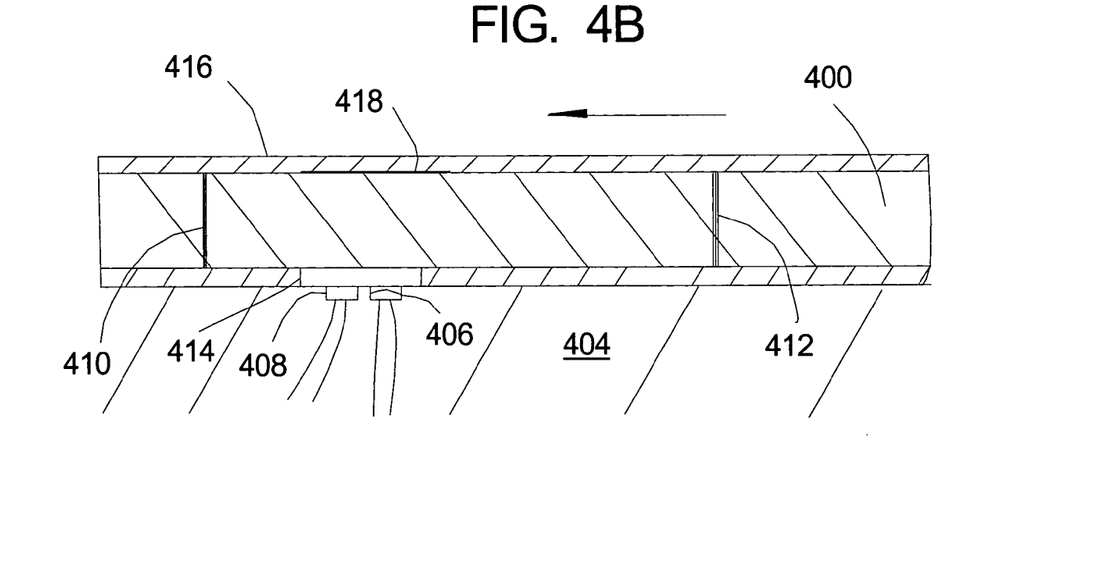
FIG. 4B illustrates a two-dimensional side view of still another embodiment of the measurement means.

Another embodiment is shown in FIGS. 4A and 4B wherein optical fiber 400, by itself, is inserted through glass tube 402. The optical fiber 400 is considered to be of conventional design having a core and cladding thereon, not shown. Optical mouse 404, only partially shown, has a light source 406 such as a LED or a laser source and a light detector 408 thereon. Glass tube 402 is mounted directly over light source 406/detector 408 combination to maximize the amount of light reflected into detector 408 so that movement of optical fiber 400 is detected. It is to be understood that the surface of optical fiber 400 has a uniform textured surface as well as cladding and/or core having a uniform "textured" material to be able to be detected by detector 408. The movement of optical fiber 400 therethrough is thus detected. Upon initiation of laser radiation through optical fiber 400, the user may click the mouse to initialize the position of optical fiber 400. Movement information is then communicated to control unit 115 providing information as to the position of optical fiber 400, i.e., the optical fiber output tip, not shown, as well as speed of optical fiber 400. This information would be used to insure that an appropriate laser energy is provided to that location as preprogrammed by the user. Further, a visual display of the treated vein may be provided to the user where the user is able to view the progress of the laser beam through the vein. For example, a changing color on the visual display would inidicate no treatment to a fully treated vein.

Further, another embodiment is shown in FIG. 4B wherein optical fiber 400 has one or more rings 410 and 412. A first ring 410 may be used to initiate laser treatment and last ring 412 may be used to cease laser treatment or to turn off the laser before the optical fiber is withdrawn totally as a safety precaution. Further, the rings may only serve as visual indications of the position of the fiber 400. Further, a window 414 in tube 416 may be placed directly over the source 406/detector 408 to again maximize the amount of light provided to optical fiber 400 for detection. Additionally, a reflective surface 418 may be attached to the inside of tube 416 to further insure that a maximum of amount of radiaton is returned to detector 408.

Another advantage of the present invention is that the practitioner has greater control over the procedure while being able to ensure that consistent doses are applied. The practitioner has the option of speeding or slowing pullback for any reason, including possible discomfort of the patient, and may also discontinue irradiation at any time by halting the pullback completely.

The present invention is ideally suited for use in conjunction with underskin or intralumenal therapeutic radiation devices, such as the underskin treatment device described in U.S. Pat. No. 6,200,332 by Del Giglio.

The present invention is further illustrated by the following example, but is not limited thereby.

Example 1

In the treatment of varicose veins, the size of the optical fiber used will vary depending on the diameter of the vein to be treated. To treat veins up to 3 or 4 mm in size, a 400-micron optical fiber is inserted into the vein. For veins greater than 4 mm a 600-micron fiber is used.

The laser is set on continuous pulse mode with a working time of 0.3 seconds and an idle time of 0.3 seconds. The laser output power is varied depending upon vein size. For a vein less than 4 mm in diameter, 7-10 joules of power is needed; for veins greater than 4 mm in diameter, 12-15 joules are needed.

Prior to treatment, abnormal lengths of the vein are identified from prior examinations. Power requirements as described above and a preferred pull-out speed is determined. Local anesthetic is then applied along the marked line of treatment. Next, the course of the vein is detected and treated as follows: the optical fiber is inserted into the vein and the laser is set to single pulse mode. Laser power is then administered: a series of 10-15 flashes are sufficient to create a scar that closes off the vein. Next, the laser setting is changed to continuous pulse mode. The optical fiber is retracted and is free to flash the inside wall of the vein and its blood contents. The control unit measures the pull-out speed based on a series of markings along the length of the fiber, and adjusts the pulse rate based on the preferred pull-out speed. In this way, consistent power is administered and a continuous coagulation line is created inside the vein. The laser flash specially effects the blood by creating a micro bubble explosion destroying the vein, which, when healing will form a thin fibrosis later to be absorbed.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A power regulated medical radiation treatment system for underskin treatments comprising:
   a radiation source;
   at least one radiation delivery system coupled to said radiation source, and comprising means to irradiate an underskin treatment area at said delivery system's distal end having an output tip;
   means for introducing at least one radiation delivery system's distal end under a patient's skin;
   means for optically measuring speed of movement of said output tip of said irradiation means relative to said underskin treatment area, wherein the means for optically measuring speed of movement comprises a light source and an optical light sensor, said irradiation means being adapted to be moved manually in said underskin treatment area during treatment; and means for controlling a parameter of radiation emitted by said source as a function of said speed of movement of said irradiation means, wherein said means for controlling a parameter of radiation emitted by said source as a function of said speed of movement of said irradiation means is a microprocessor or a computer.

2. The power regulated medical radiation treatment system according to claim 1, wherein said radiation source is selected from a group consisting of a laser source, a high power lamp, a laser diode, a light-emitting diode, and a diode array.

3. The power regulated medical radiation treatment system according to claim 1, wherein said radiation delivery system is selected from the group consisting of an optical fiber and a catheter system containing an optical fiber.

4. The power regulated medical radiation treatment system according to claim 1, wherein said output tip is selected from a group consisting of a bare fiber tip, a shaped fiber tip, and a diffuser tip.

5. The power regulated medical radiation treatment system according to claim 1, wherein said parameter of said radiation is selected from the group consisting of power level, pulse length and pulse rate.

6. The power regulated medical radiation treatment system according to claim 3, wherein said measurement means comprises periodic marks on an exterior surface of said optical fiber.

7. The power regulated medical radiation treatment system according to claim 3, wherein said optical light sensor captures sequential images of a surface of said radiation delivery system;

said means for measuring speed of movement of said irradiation means being based on changes in said surface of said radiation delivery system, observable optically; and wherein said means to measure speed of movement of said irradiation means is stationary with respect to said irradiation means, being connected to a proximal end of said means for introducing at least one radiation delivery system's distal end under a patient's skin.

8. The power regulated medical radiation treatment system according to claim 7, wherein said light source is a laser diode.

9. The power regulated medical radiation treatment system according to claim 1, wherein said control means is connected to said measurement means to receive information from said measurement means, convert said information into and a speed value, and alter radiation power from said source based upon preselected parameters to obtain a desired power density.

10. The power regulated radiation treatment system according to claim 1, wherein said radiation delivery system is selected from the group consisting of an optical fiber and a catheter system containing an optical fiber, said means to optically measure speed includes an optical computer mouse adapted to respond to movement of said optical fiber, and said means to control a parameter of radiation as a function of speed of movement includes presenting visual information to an operator of said treatment system regarding said speed.

\* \* \* \* \*